(12) United States Patent
Keller

(10) Patent No.: US 7,169,153 B2
(45) Date of Patent: Jan. 30, 2007

(54) SURGICAL INSTRUMENT FOR INSERTING INTERVERTEBRAL PROSTHESIS

(75) Inventor: Arnold Keller, Kayhude (DE)

(73) Assignee: DePuy Spine, Raynham, MA (US)

( * ) Notice: Subject to any disclaimer, the term of this patent is extended or adjusted under 35 U.S.C. 154(b) by 414 days.

(21) Appl. No.: 10/358,392

(22) Filed: Feb. 5, 2003

(65) Prior Publication Data

US 2003/0229355 A1    Dec. 11, 2003

(30) Foreign Application Priority Data

Jun. 10, 2002    (DE) ............................. 102 25 703

(51) Int. Cl.
*A61B 17/60*    (2006.01)

(52) U.S. Cl. ..................................... 606/99

(58) Field of Classification Search .................. 606/90, 606/99, 86, 205, 206, 207, 208
See application file for complete search history.

(56) References Cited

U.S. PATENT DOCUMENTS

| | | | |
|---|---|---|---|
| 6,551,316 B1 * | 4/2003 | Rinner et al. .................. 606/57 |
| 6,716,218 B2 * | 4/2004 | Holmes et al. .............. 606/105 |
| 2002/0116009 A1 * | 8/2002 | Fraser et al. .................. 606/99 |
| 2004/0002758 A1 * | 1/2004 | Landry et al. ........... 623/17.11 |
| 2004/0093021 A1 * | 5/2004 | Hanson ....................... 606/208 |
| 2004/0106927 A1 * | 6/2004 | Ruffner et al. ................. 606/90 |

FOREIGN PATENT DOCUMENTS

| | | |
|---|---|---|
| DE | 299 16 078 U1 | 12/1999 |
| DE | 198 36 498 A1 | 2/2000 |
| DE | 200 04 812 U1 | 11/2000 |
| DE | 201 16 410 U1 | 1/2002 |
| EP | 0 269 935 A2 | 6/1988 |
| EP | 0 333 990 A2 | 9/1989 |

* cited by examiner

*Primary Examiner*—Eduardo C. Robert
*Assistant Examiner*—James L. Swiger
(74) *Attorney, Agent, or Firm*—Dickstein Shapiro LLP

(57) ABSTRACT

Surgical instrument for inserting an intervertebral prosthesis, having first and second prosthesis holders (52A, 52B) for a pair of prosthesis plates, which holders are connected to one another by a parallel guide (57) and can be spread by a lever arrangement (131). The first of the prosthesis holders is arranged on an elongate instrument body in order to give the surgeon an exact picture of the orientation of the prosthesis and to allow force to be exerted in exactly this direction. The actuating lever (131) is articulated with its front end on the second prosthesis holder (52B) so as to pivot about a spindle (130) extending transversely with respect to the longitudinal direction of the instrument body (51) and to the direction of spreading. Behind this spindle (130), it has a limit stop (133) which acts directly or indirectly on the instrument body (51) or the first prosthesis holder (52A). The lever arrangement can also be the other way around.

19 Claims, 4 Drawing Sheets

SURGICAL INSTRUMENT FOR INSERTING INTERVERTEBRAL PROSTHESIS

BACKGROUND OF THE INVENTION

To insert intervertebral prostheses consisting of two prosthesis plates, each to be connected to a respective vertebral body, and of a prosthesis core arranged between these plates, insertion instruments are known (EP-A-333 990) which, at their front end, have two prosthesis holders which each receive a prosthesis plate. The prosthesis holders are connected to one another via a parallel guide which makes it possible initially to bring the prosthesis plates very close to one another, so as to be able more easily to introduce them into the narrow intervertebral space, and then to spread them apart with the adjoining vertebrae in order to be able to insert the prosthesis core between them. Thereafter, the prosthesis holders are moved back toward one another so that the prosthesis plates receive and securely hold the prosthesis core, and the instrument is removed. The known instrument is designed as a forceps which is angled in relation to the direction of the prosthesis holders, which direction is intended to coincide with the median direction of the body. The use of forceps has the disadvantage that the forceps bows which the operating surgeon holds in the hand do not give him an exact picture of the orientation of the front end of the forceps and of the prosthesis to be inserted. A similar instrument (DE-U-201 16 410) is used for introducing and spreading a total prosthesis.

An instrument for introducing a prosthesis is also known (DE-U-299 16 078) which is formed by a lower pair of guide rods and an upper guide rod, these rods being articulated on one another at the rear end and carrying prosthesis holders at their front ends. They form a guide track for a spreader element. When the latter is driven forward between them by means of a toothed rack, it spreads the rod ends apart and at the same time pushes the prosthesis core ahead of it until the latter has reached the desired end position. Thereafter, the spreader element is drawn back in order to bring the prosthesis plates toward the prosthesis core. In this case, the spreading movement is inextricably linked with the introduction of the prosthesis core, so that the spreading operation is not separate from the introduction of the prosthesis core and can be observed only with difficulty.

Instruments whose purpose is only to spread the vertebrae apart are also known. One of these known instruments (DE-U-200 04 812) has, at the front end of an elongate instrument body, two spreader members which are connected by a parallel guide and can be spread via a push rod, extending within the instrument body, and via toggle levers. The push rod is actuated by a forceps-like auxiliary instrument. This arrangement is complicated. In another known instrument (DE-A-198 36 498, FIGS. 5 and 6), two spreader members are connected to one another via a parallel guide and can be spread apart from one another by a transversely extending threaded rod. As this threaded rod can be actuated only with difficulty within the operating site, a design is instead recommended (FIG. 1) in which the spreader members are arranged on a forceps, and a parallel guide is dispensed with. Finally, a spreading forceps is known (EP-A-269935) in which one of two spreader members connected by a parallel guide is connected to one shank of a spreading forceps, while the other shank is articulated on the other spreader member. The spreader members comprise pins which are fitted into bores of the vertebral bodies which are to be spread apart. The vertebral bodies are thereby weakened. The use of a forceps also has the disadvantage that the forceps bows do not give the operating surgeon an exact picture of the orientation of the prosthesis.

SUMMARY OF THE INVENTION

The object of the invention is to make available an instrument for inserting an intervertebral prosthesis, which instrument gives the operating surgeon an exact picture of the orientation of the prosthesis parts held by the instrument, comprises what, from the point of view of the operating surgeon, are simple and easy-to-see elements, and is easy to operate.

The invention starts out from the known instrument mentioned at the outset, in which two prosthesis holders are provided which are connected to one another via a parallel guide and can be spread apart from one another by a lever arrangement. According to the invention, the first of the two prosthesis holders is arranged on an elongate instrument body. The direction of the instrument body gives the operating surgeon at all times an exact picture of the orientation and position of the implant. The lever arrangement comprises an actuating lever which at its front end is articulated pivotably on the instrument body or the first prosthesis holder. The pivot axis extends transversely with respect to the longitudinal direction of the instrument body and to the direction of spreading. Behind this axis, the lever has a limit stop which acts directly or indirectly on the second prosthesis holder. At the rear end, the lever is designed in such a way that it can be operated by hand. In the unspread state of the instrument, the lever is at a certain angular distance from the instrument body. If it is pulled by hand, or by suitable aids such as a threaded spindle, toward the instrument body, the limit stop moves the second prosthesis holder away from the first prosthesis holder and in this way spreads them apart. By virtue of the lever action, great spreading forces can be transmitted.

In an alternative embodiment which constitutes the reversal of the aforementioned arrangement, the front end of the actuating lever is articulated on the second prosthesis holder and its limit stop acts on the instrument body or the first prosthesis holder.

In a further embodiment of the invention, the limit stop acts on an oblique link arm which is connected to the second prosthesis holder and can be part of the parallel guide.

In an expedient configuration, the lever is not an integral component part of the instrument body, but instead is designed in such a way that it can be attached to the instrument body, and again released from it, during the operation. This has the advantage that the instrument body is not impeded by the spreading mechanism, formed by the lever, in those stages of the operation where spreading does not take place or does not have to be maintained. If the actuating lever is articulated on one of the two movable elements and acts on the other element via a limit stop, a longitudinal displacement may occur at the limit stop, between the limit stop and the limit stop mating surface, through which undesired frictional forces are generated. According to a further feature of the invention, provision is therefore made for the limit stop to act on the limit stop mating surface via a friction-reducing means. This friction-reducing means can, for example, be formed by a roller which is provided on the limit stop or on the mating surface for the limit stop. A linkage articulated at one end on the limit stop and articulated at the other end on the other element can also be used as a friction-reducing means.

After the prosthesis-plates have been introduced in the intended position into the intervertebral space and have been spread apart, the prosthesis core connecting the prosthesis plates can be inserted. To do this, an insertion instrument is used which, for example, is designed as a forceps and which at its front end grips the prosthesis core. So that the operating surgeon, when introducing the prosthesis core, can easily find the position of the prosthesis core holder in which the prosthesis core has reached the desired position between the prosthesis plates, the insertion instrument for the prosthesis plates and the prosthesis core holder are expediently provided with interacting limit stops which define this end position.

BRIEF DESCRIPTION OF THE DRAWINGS

The invention is explained in greater detail below with reference to the drawing which depicts advantageous illustrative embodiments. In said drawing.

DETAILED DESCRIPTION OF THE INVENTION

Figure 1:
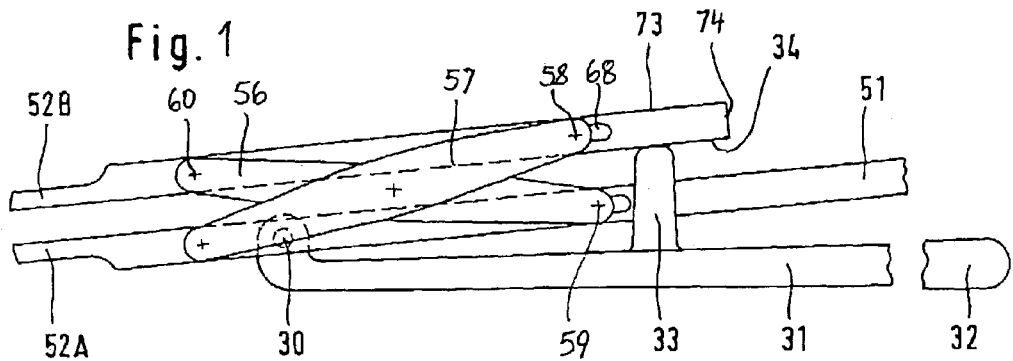
FIG. 1 shows a side view of the front part of a first embodiment.

At the front end of the instrument body 51 there are two holders 52A and 52B for prosthesis plates 53. The prosthesis holders 52 are fork-shaped and open at the end. Their side branches form guides for the edge of the prosthesis plates 53. Their direction coincides with the longitudinal direction of the instrument body. This has the advantage that the operating surgeon is at all times aware of the orientation of the prosthesis plates, and that the force necessary for driving the prosthesis plates in can be exerted in the instrument direction. By overcoming a frictional force, the prosthesis plates can be inserted into the prosthesis holders 52, and made to slide out of said prosthesis holders 52, in the longitudinal direction of the instrument. At the rear end, the prosthesis body 51 has a strike plate 54. By striking this plate, the prosthesis plates 53 held by the prosthesis holders 52 can be driven in between two vertebral bodies when the prosthesis holders 52 are not spread apart and the prosthesis plates lie against one another.

The lower prosthesis holder 52A is securely connected to the instrument body 51, and if appropriate made integral therewith. The upper prosthesis holder 52B is connected to the instrument body 51 via a scissor arrangement consisting of scissor members 56, 57. The scissor arrangement 56, 57 is provided as a pair on both sides of the instrument body and is designed in such a way that the upper prosthesis holder 52B can move exclusively perpendicular to the lower prosthesis holder 52A and parallel to it. The prosthesis holders can be brought very close to one another, if appropriate without any spacing between them, so that it is easier to drive them into the intervertebral space. They can be spread apart (FIG. 3) together with the adjoining vertebral bodies in order to create space for introducing a prosthesis core 77 between the prosthesis plates 53. They are then brought back toward each other in order to secure the prosthesis core in the desired position. The instrument can then be removed.

The rear pins 58, 59 of the scissor members 56, 57 slide in oblong holes 68 of the instrument body 51 or of the plate 73 belonging to the upper prosthesis holder 52B. The direction of the oblong holes coincides with the longitudinal direction of the instrument. The front pins 60 of the scissor members 56, 57 are mounted with a fixed axis on the prosthesis holders 52.

In the spread-apart state, a channel-like free space is formed between the instrument body 51 and the plate 53 continuing the upper prosthesis holder 52 rearward, on the one hand, and between the lateral scissor arrangements 56, 57 on the other hand. Using a prosthesis core holder guided between the link arms 56, 57, the prosthesis core 77 can be guided through this free space between the prosthesis plates. The prosthesis core holder has a limit stop 75 which bears on the rear edge 74 of the plate 73 when the prosthesis core 77 has exactly reached the intended position between the prosthesis plates.

According to FIG. 1, the instrument body 51, near its front end, is connected via a pivot spindle 30 to the front end of an actuating lever 31 which extends approximately parallel to the instrument body 51 and which, at its rear end 32, can be gripped in the manner of a forceps lever so as to be pressed onto the instrument body 51. It has a limit stop projection 33, or a pair of limit stop projections 33 situated on both sides of the instrument body and extending toward a mating limit stop surface 34 of the second prosthesis holder or of the plate 73 connected to this. When the prosthesis holders 52A, 52B are not spread apart, the actuating lever 31 extends at an acute angle from the instrument body 51. When it is pressed onto the instrument body 51, the limit stop projection 33 lifts the prosthesis holder 52A in order to spread it apart from the prosthesis holder 52A.

Figure 2:
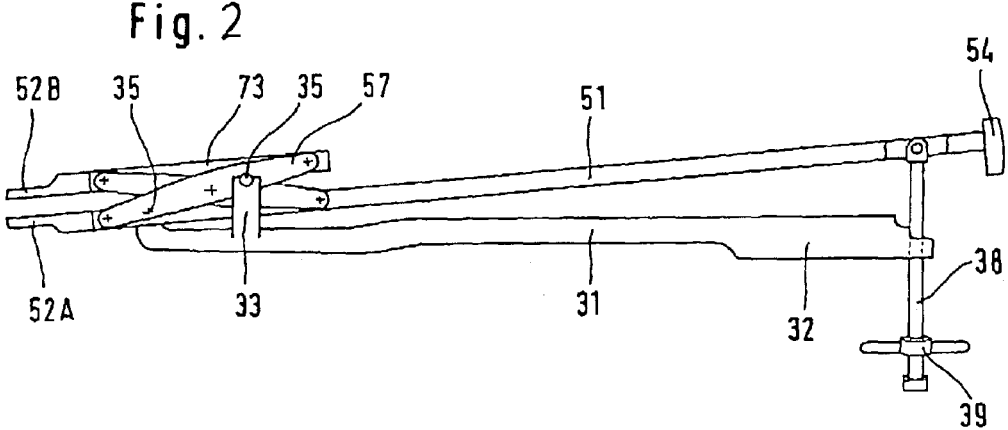
FIG. 2 shows the side view of a second embodiment.
Figure 3:
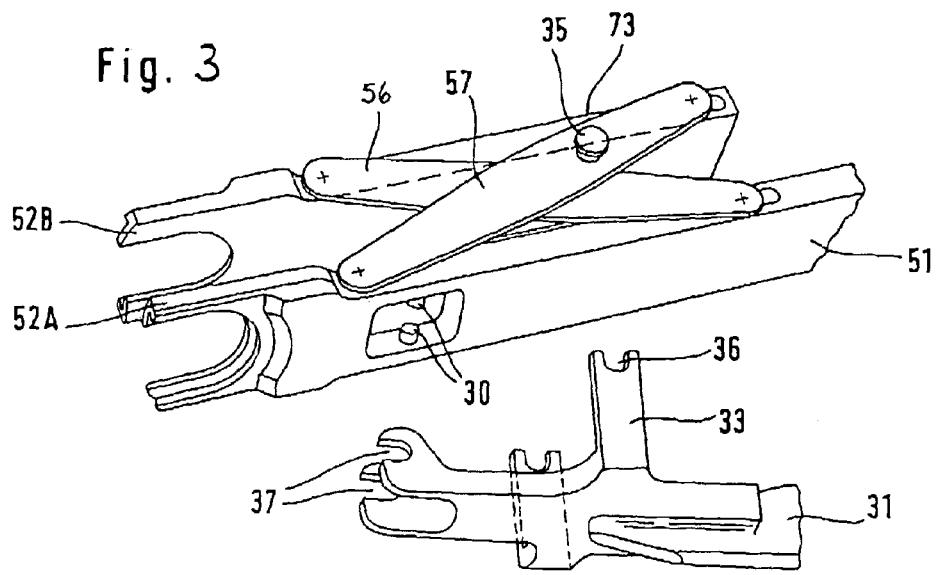
FIG. 3 shows the perspective view of the front part of the second embodiment.
Figure 4:
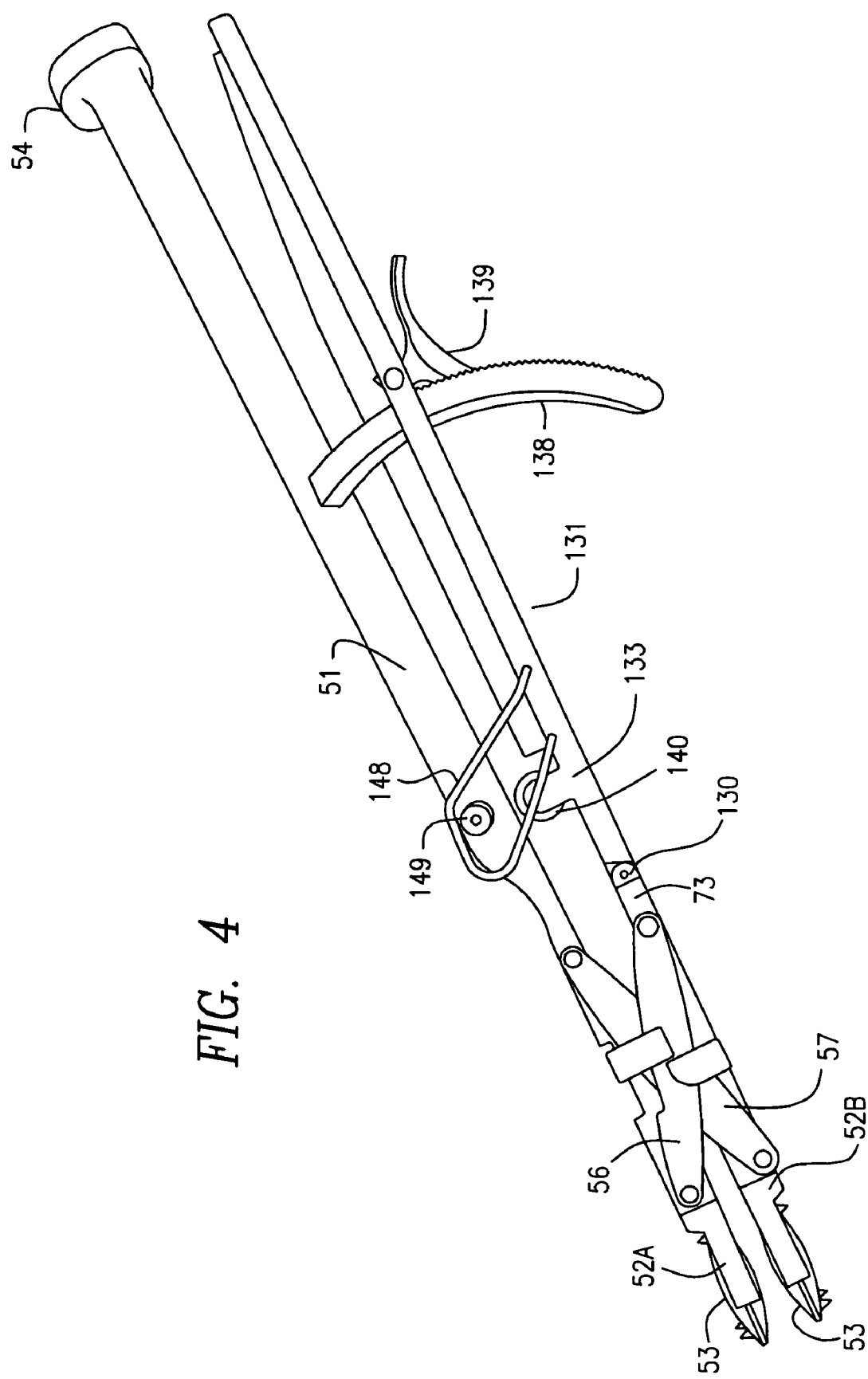
FIG. 4 shows the general view of a third embodiment of the instrument.
Figure 5:
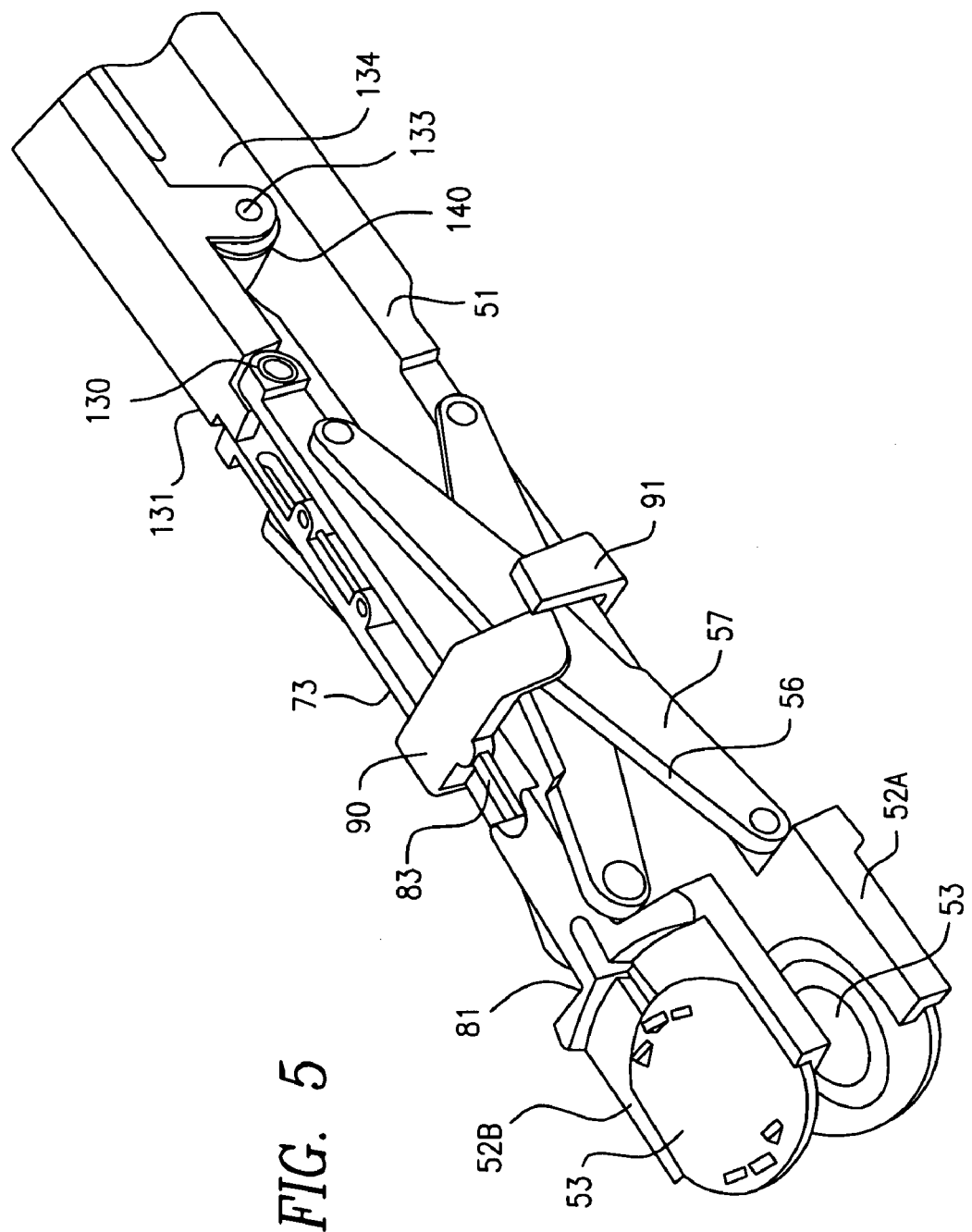
FIG. 5 shows a perspective view of the front part of the third embodiment.

A similar, second embodiment is shown in FIGS. 2 and 3. Identical reference numbers denote identical parts. For the description of these parts, reference can be made to the above example, unless otherwise stated below. The limit stop projection 33 does not engage directly on the plate 73, but instead engages on the link arm 57 which carries a limit stop pin 35 interacting with a recess 36 at the end of the limit stop projection 33. To interact with the spindle 30, a bearing cutout 37 open at one end is provided at the end of the actuating lever 31. The mode of functioning is the same as that in the illustrative embodiment in FIG. 1. The difference lies in the fact that, by means of the engagement of the limit stop projection 33 on the oblique link arm 57, a transmission is obtained whose magnitude can be freely determined by the choice of the engagement point. The embodiment according to FIG. 9 also differs from that according to FIG. 1 in that the actuating lever 31, by virtue of the open recess 36 and of the bearing cutout 37 open at one end, can be easily released from the instrument body or easily coupled to the latter during the operation. As can be seen in FIG. 3, the limit stop projection 33, the limit stop pin 35, the spindle 30 and the bearing cutout 37 open at the end are provided in pairs so as to permit a symmetrical connection with the instrument body and so that the space between the parallel guides 56, 57 which is used for insertion of the prosthesis core is kept free of structural parts.

At the rear end 32, the actuating lever 31 can of course be operated by hand. In addition, a threaded spindle 38 is provided on which the actuating lever 31 can be brought close to the instrument body 51 with considerable force by means of a nut 39 and with the aid of which the spread position of the instrument can be secured. The actuating lever 31 can also be released from the instrument body in the area of the spindle 38.

The description of the first and second embodiments also applies to the third embodiment, except where stated below. The same reference numbers are also used. This illustrative embodiment has the advantage that the instrument can be made very narrow. The instrument body 51 ends at the front in the holder 52A for a prosthesis plate 53. The rear part 73 of the upper prosthesis holder 52B is connected to the instrument body 51 by a parallel guide with link arms 57. The prosthesis holders 52 include a slide 81 which, by means of a handle (not shown), can be pushed forward via a rod 83 and limit stop branches 90, 91 and via a push rod 86 (not shown) mounted in the instrument body 51, in order to push the prosthesis plates located in the holders 52 out forward and to draw the instrument back so as to free it from the insertion position.

At the rear end of the upper prosthesis holder 52B, an actuating lever 131 is articulated, at 130, about an axis perpendicular to the direction of the instrument body 51 and to the direction of spreading.

A few centimeters behind this, the actuating lever 131 has a projection 133 which protrudes toward the instrument body 51 and has a rotatably mounted roller 140 at its end. The limit stop projection 133 bears with this roller on the mating surface 134 of the instrument body 51. If the actuating lever 31 is moved toward the instrument body 51, the upper prosthesis holder 52B is lifted relative to the instrument body 51 and relative to the lower prosthesis holder 52A, as a result of which the instrument holders are spread apart from one another. The spread position can be secured, and then released again, by means of a catch mechanism 138, 139.

The prosthesis holders 52 must not be allowed to spread apart accidentally. This applies in particular to the stage of the operation prior to insertion of the prosthesis holders into the intervertebral space. For this purpose, a fixture consisting of slotted guide 148 and slide block 149 is provided which holds the limit stop 133 so that the latter essentially bears on the limit stop mating surface 134. In conjunction with the catch mechanism 138, 139, the prosthesis holder 52B is thus secured in the particular position assigned to it. This also applies when the instrument comes into a position in which the prosthesis holder 52B is arranged lower than the prosthesis holder 52A and therefore tends to move away from the latter under the effect of gravity.

Figure 6:
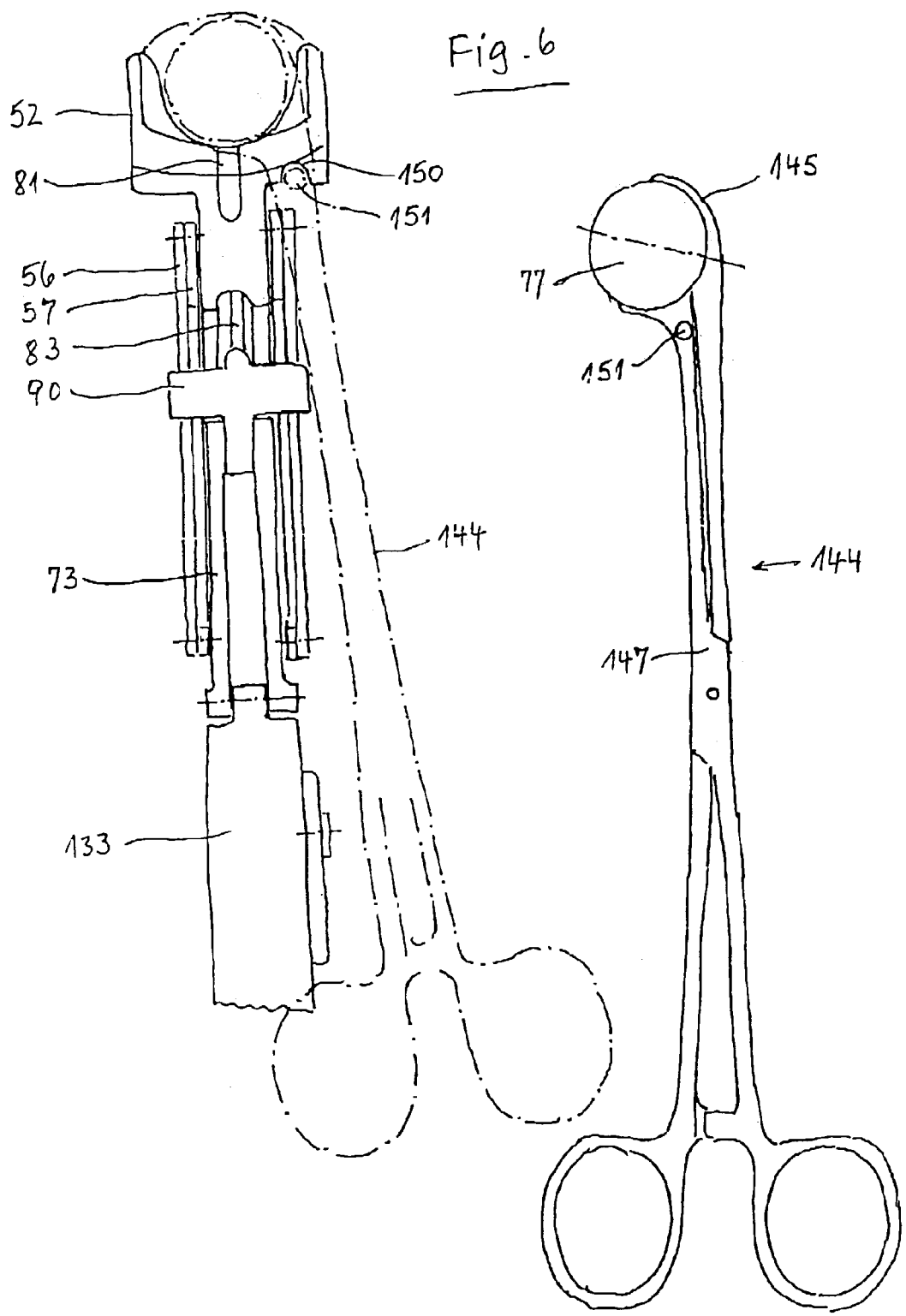
FIG. 6 shows the diagrammatic representation of the interaction of the third embodiment of the instrument with a prosthesis core holder.

As soon as the prosthesis plates have been introduced into the intervertebral space and spread apart, the prosthesis core is fitted. This is done using the forceps 144 shown in FIG. 6 and also referred to in the present text as the prosthesis core holder. It is distinguished by the particular feature that the holder 145 which is formed at the front end for the prosthesis core 146 is offset laterally, as viewed from the direction of the elongate instrument body 147, and also opens obliquely to the side in the direction of the dot-and-dash line. By this means it is possible to introduce the prosthesis core holder into the operation opening essentially parallel to the insertion instrument, also to open it in this setting when the prosthesis core has reached the intended position, and also to remove it again in this setting.

Because the operating site is difficult to see, and the operating surgeon cannot therefore easily discern by sight whether the prosthesis core has reached the intended position between the prosthesis plates, the insertion instrument and the prosthesis core holder are equipped with interacting limit stops which come into engagement with one another when the end position of the prosthesis core is reached. In the present example, these limit stops are designed as a notch 150 on the insertion instrument and a pin 151 on the prosthesis core holder. The operating surgeon guides the prosthesis core holder along the insertion instrument and into the operation opening until the pin 151 has reached the notch 150. The operating surgeon can easily feel when these two elements have engaged. He then knows that the prosthesis core is located in the intended position between the prosthesis plates. He will then reverse the spreading of the prosthesis plates until the prosthesis core is securely gripped, and he will then withdraw the prosthesis core holder.

The invention claimed is:

1. Surgical instrument for inserting intervertebral prostheses, having a first prosthesis holder and a second prosthesis holder for a pair of prosthesis plates, which holders are connected to one another by a parallel guide and can be spread by means of a lever arrangement, characterized in that the first prosthesis holder is arranged on an elongated instrument body and the lever arrangement comprises an actuating lever which is articulated at its front end on the first prosthesis holder so as to pivot about a spindle, said spindle extending transversely with respect to the longitudinal direction of the instrument body and to the direction of spreading, and behind this spindle it has a limit stop which acts directly or indirectly on the second prosthesis holder.

2. Instrument according to claim 1, characterized in that the limit stop acts on an oblique link arm which is part of the parallel guide.

3. Instrument according to claim 1, characterized in that the actuating lever can be easily attached or released during the operation.

4. Instrument according to claim 1, characterized in that the limit stop acts, via a friction-reducing means, on a limit stop mating surface on the instrument body or on the first or second prosthesis holder.

5. Instrument according to claim 4, characterized in that a fixture pairing is provided which comprises a slotted guide and slide block and holds the limit stop on the limit stop mating surface.

6. Instrument set with an instrument according to claim 1, characterized in that a prosthesis core holder is provided and the instrument and the prosthesis core holder have interacting limit stops for determining the end position of the prosthesis core holder.

7. Instrument set according to claim 6, characterized in that the prosthesis core holder has an elongated instrument body and at its front end has an angled holder opening to the side for the prosthesis core.

8. Instrument for inserting an intervertebral prosthesis, having a first prosthesis holder and a second prosthesis holder for a pair of prosthesis plates, which holders are connected to one another by a parallel guide and can be spread by means of a lever arrangement, characterized in that the first prosthesis holder is arranged on an elongate instrument body and the lever arrangement comprises an actuating lever which is articulated at its front end on the second prosthesis holder so as to pivot about a spindle extending transversely with respect to the longitudinal direction of the instrument body and to the direction of spreading, and behind this spindle it has a limit stop which acts directly or indirectly on the instrument body or the first prosthesis holder, and the limit stop acts, via a friction-reducing means, on a limit stop mating surface on the instrument body or on the first or second prosthesis holder, and a fixture pairing is provided which comprises a slotted guide and slide block and holds the limit stop on the limit stop mating surface.

9. Instrument according to claim 8, characterized in that the limit stop acts on an oblique link arm which is part of the parallel guide.

10. Instrument according to claim 8, characterized in that the actuating lever can be easily attached or released during the operation.

11. Instrument according to claim 8, characterized in that the limit stop acts, via a friction-reducing means, on a limit stop mating surface on the instrument body or on the first or second prosthesis holder.

12. Instrument for inserting an intervertebral prosthesis, having a first prosthesis holder and a second prosthesis holder for a pair of prosthesis plates, which holders are connected to one another by a parallel guide and can be spread by means of a lever arrangement, characterized in that the first prosthesis holder is arranged on an elongate instrument body and the lever arrangement comprises an actuating lever which is articulated at its front end on the second prosthesis holder so as to pivot about a spindle extending transversely with respect to the longitudinal direction of the instrument body and to the direction of spreading, and behind this spindle it has a limit stop which acts directly or indirectly on the instrument body or the first prosthesis holder, and a prosthesis core holder is provided and the instrument and the prosthesis core holder have interacting limit stops for determining the end position of the prosthesis core holder.

13. Instrument set according to claim 12, characterized in that the prosthesis core holder has an elongated instrument body and at its front end has an angled holder opening to the side for the prosthesis core.

14. Instrument according to claim 13, characterized in that the limit stop acts, via a friction-reducing means, on a limit stop mating surface on the instrument body or on the first or second prosthesis holder.

15. Instrument according to claim 13, characterized in that the limit stop acts on an oblique link arm which is part of the parallel guide.

16. Instrument according to claim 13, characterized in that the actuating lever can be easily attached or released during the operation.

17. Instrument according to claim 12, characterized in that the limit stop acts on an oblique link arm which is part of the parallel guide.

18. Instrument according to claim 12, characterized in that the actuating lever can be easily attached or released during the operation.

19. Instrument according to claim 12, characterized in that the limit stop acts, via a friction-reducing means, on a limit stop mating surface on the instrument body or on the first or second prosthesis holder.

\* \* \* \* \*